Figure 1:
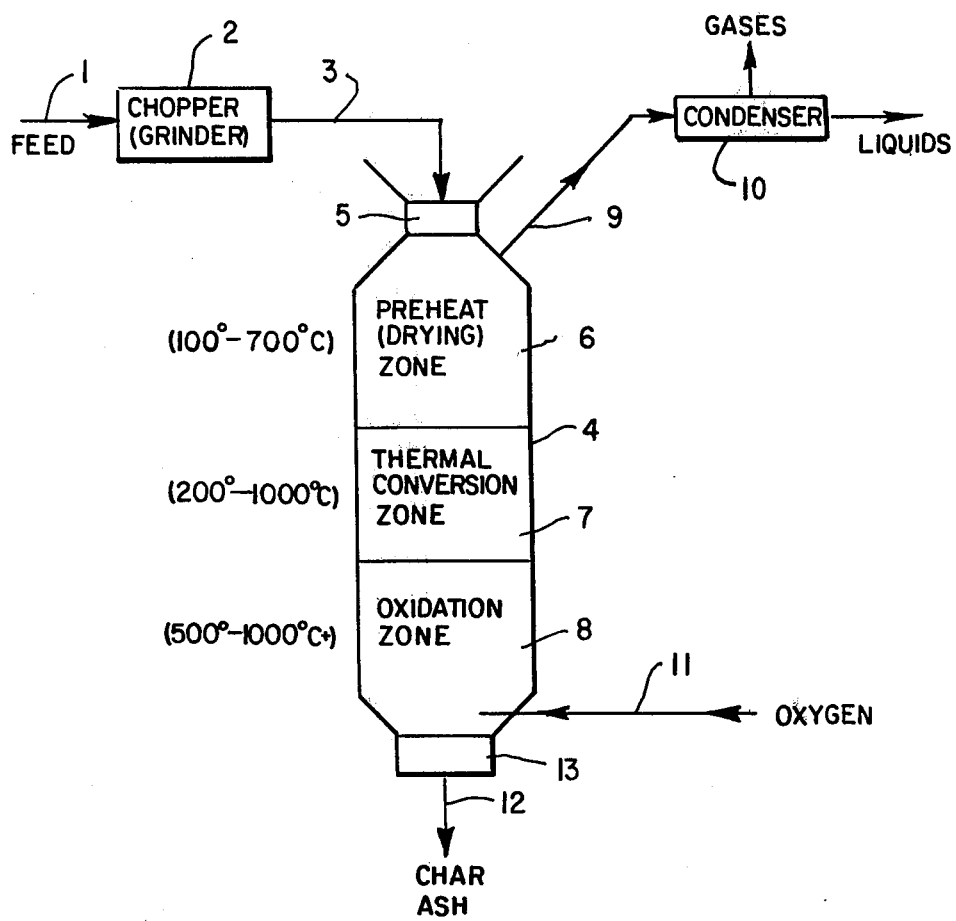

United States Patent [19]

Weil et al.

[11] 4,313,011
[45] Jan. 26, 1982

[54] PLANT HYDROCARBON RECOVERY PROCESS

[75] Inventors: Thomas A. Weil, Naperville; Peter M. Dzadzic, Lisle; Chien-Cheng J. Shih, Naperville; Michael C. Price, West Chicago, all of Ill.

[73] Assignee: Standard Oil Company (Indiana), Chicago, Ill.

[21] Appl. No.: 138,541

[22] Filed: Apr. 9, 1980

[51] Int. Cl.$^3$ .................. C07C 1/00; C07C 4/00; C10G 1/00

[52] U.S. Cl. .................. 585/240; 48/209; 201/2.5; 201/8; 201/25; 208/7; 208/8 R; 585/408; 585/469; 585/638; 585/733

[58] Field of Search .............. 585/240, 408, 469, 638, 585/733; 48/209; 208/7, 8 R; 201/2.5, 8, 25

[56] References Cited

U.S. PATENT DOCUMENTS

| | | | |
|---|---|---|---|
| 2,151,166 | 3/1939 | Slatineanu | 585/240 |
| 2,495,396 | 1/1950 | Urison et al. | 585/240 |
| 2,551,579 | 5/1951 | Berl | 585/20 |
| 3,223,698 | 12/1965 | Oshima et al. | 585/240 |
| 4,102,938 | 7/1978 | Rao | 585/240 |
| 4,105,502 | 8/1978 | Choi | 201/2.5 |
| 4,118,282 | 10/1978 | Wallace | 201/2.5 |

FOREIGN PATENT DOCUMENTS 424847 3/1935 United Kingdom .............. 585/240

*Primary Examiner*—Curtis R. Davis
*Attorney, Agent, or Firm*—William C. Clarke; William T. McClain; William H. Magidson

[57] ABSTRACT

A process for production and recovery of hydrocarbons from hydrocarbon-containing whole plants in a form suitable for use as chemical feedstocks or as hydrocarbon energy sources which process comprises: (a) pulverizing by grinding or chopping hydrocarbon-containing whole plants selected from the group consisting of Euphorbiaceae, Apocynaceae, Asclepiadaceae, Compositae, Cactaceae and Pinaceae families to a suitable particle size, (b) drying and preheating said particles in a reducing atmosphere under positive pressure (c) passing said particles through a thermal conversion zone containing a reducing atmosphere and with a residence time of 1 second to about 30 minutes at a temperature within the range of from about 200° C. to about 1000° C., (d) separately recovering the condensable vapors as liquids and the noncondensable gases in a condition suitable for use as chemical feedstocks or as hydrocarbon fuels.

14 Claims, 1 Drawing Figure

PLANT HYDROCARBON RECOVERY PROCESS

BACKGROUND OF THE INVENTION

This invention relates to a process for the production and recovery of hydrocarbon chemical feedstocks and hydrocarbon fuels from renewable plant sources using whole plants.

In the prior art, industrial, farm and household wastes have been taught as sources for recovery of organic compounds by heating in the presence or absence of oxygen. The presence of oxygen causes the reactor product to contain significant amounts of carbon dioxide and water. If oxygen is not used to maintain combustion, an indirect method of heating typically is used with consequent problems of heat transfer. For example, U.S. Pat. No. 3,639,111 teaches a method and apparatus for destructively distilling kraft black liquor, garbage, and organic wastes at an elevated temperature and a controlled amount of oxygen insufficient for complete combustion, the elevated temperature being above a critical temperature zone, thereby reducing or cracking gases from the material to stable end products, the temperature being maintained to preclude recombination of intermediate products. The cracking products are hydrogen, carbon monoxide and methane. Sulfur compounds are scrubbed out as hydrogen sulfide. U.S. Pat. No. 3,718,446 teaches the pyrolysis of kraft black liquor, garbage, and organic wastes at a sufficiently high temperature (of 800° C. to 1,200° C. or higher) and for a sufficient length of time (of from 1 to 30 seconds) to prevent recombination reactions and produce stable products such as aromatic phenols, hydrogen, carbon monoxide, carbon dioxide and methane. Gaseous emissions from the pulping operation are the source of oxygen. U.S. Pat. No. 3,729,298 teaches a process for disposing of solid refuse by thermally decomposing it in a shaft furnace with temperatures on the order of 3000° F. and simultaneously producing a fuel or synthesis gas primarily containing over 50% carbon monoxide by combusting the char and hydrogen. A gas containing at least 40% oxygen is fed into the furnace to create a thermal driving force in excess of 1600° F. A reducing atmosphere in the hearth is taught to prevent over-oxidation of the char to $CO_2$ and oxidation of the metallic components of the refuse although the process can be operated under mildly oxidizing conditions. U.S. Pat. No. 3,843,457 teaches a process for microwave pyrolysis of wastes to recover vaporizable organic compounds such as organic acids and aldehydes from nominally solid organic wastes by comminuting the wastes and mixing them with a gas stream at a pressure substantially less than atmospheric. The gases are preferably reducing gases, particularly hydrogen. The comminuted wastes are subject to microwave discharge which effects molecular decomposition and the vaporized components are thereby removed from the gas stream. U.S. Pat. No. 3,983,009 teaches the destructive distillation of solid organic wastes to reduce volume and produce usable products such as oils, pyroligenous liquor, methanol, acetone, combustible gases, and a high carbon char without environmental pollution. The hot gases are fractionally distilled to remove useful products and are then recycled into the destructive distillation process with additional combustion air. U.S. Pat. No. 4,002,438 teaches a method and a device for the flash pyrolytic conversion of organic materials into gaseous or liquid fuels comprising methane, hydrogen, ethane with some light oil fractions in a single self-contained vessel wherein problems of clogging, coke formation, and sludge formation are substantially avoided by use of a mixture of dense, hard abrasion-resistant material which is recycled with recycled product gas and combustion air. U.S. Pat. No. 4,078,973 teaches a closed loop pyrolysis process for organic solid wastes wherein the heat is supplied by inert particles which are heated in a separate combustion zone. The residence time during pyrolysis is generally less than 10 seconds. The pyrolysis temperature is between 600° F. and the introduction temperature of the inert particles to the pyrolysis zone which can be between 600° F. to about 2,000° F. The carrier gases are oxygen-free. The products are carbon-containing char, pyrolytic oils of an oxygenated nature and gases primarily of the oxides of carbon and light hydrocarbons. U.S. Pat. No. 4,153,514 teaches a process for recovery of chemical values from waste solids wherein shredded waste solids are intermixed with hot char and a carrier gas and passed through a pyrolysis zone under turbulent conditions at temperatures of from 300° F. to 2000° F.

It is known also that pyrolysis of municipal waste containing cellulose can produce olefins. When finely divided cellulose-containing waste is rapidly heated to 700° C., olefins are reported as being the dominant product with a relatively dilute system and short residence times. Aromatic tars or oxygenated organics form if the reaction continues (*Chemical & Eng. News*, Oct. 1, 1979, p. 37).

In the prior art, processes have been taught for recovery of hydrocarbons from sources other than waste materials. The crushing of oil seeds to obtain vegetable oils is well-known as is also the distillation of pine stumps to obtain naval stores. Crushing combined with water extraction as well as catalytic processes are known. For example, U.S. Pat. No. 1,740,079 teaches the extraction of rubber from plants such as guayule. The guayule plants are reaped and dried, then crushed by rolls or other suitable machinery so as to open up the pith seams and break the bark. The crushed plants are cut into short pieces and soaked in water until the bark and pith are soft. The entire mass of material is then introduced into a water-filled ball mill and subjected to the action of such mill until the bark and pithy material are separated from the hard woody material. The bark and pithy material are reduced to a pulp. The rubber particles are freed from the rest of the material and are agglomerated to rise to the surface of the water for removal. As for processing the rubber from the guayule plant, it has been reported (*Chemical Engineering*, May 8, 1978, p. 100) that a major problem is that about 25% in unwanted resins normally comes out with the raw rubber. Another extraction process for recovering hydrocarbon values from whole-plant feedstock crops employs rolling mills that shear and compress plant material between dissynchronous rollers. The action of the rollers ruptures cellular material to facilitate downstream extraction with solvents in contrast to the conventional process in use which is wet milling (*Chemical Engineering*, Sept. 11, 1978, p. 101). Catalytic processes also have been developed. Hydrolyzed wood chips are converted directly to an oil by means of a sodium carbonate catalyst and biomass is converted to hydrogen, carbon monoxide and olefins to paraffinic fuels by use of a Fischer-Tropsch-type catalyst (*Chemical & Eng. News* Oct. 1, 1979, p. 35). Methods have been suggested to recover certain useful hydrocarbons from plant crops such as solvent extraction of organic materials (*Science,* 198, Dec. 2, 1977, 942–944), pyrolysis of tree bark to obtain benzene compounds (*Tr. Sib. Tekhnol. Inst.,* 1970, No. 43, 30–33; CA77:90240v), hydrolysis of carbohydrates in plant biomass to sugars for further processing (*Chemical & Eng. News,* Apr. 3, 1978, 31).

Accordingly, the prior art teaches processes wherein solid waste and waste products are used as sources of organic compounds, by decomposition, by cracking or by destructive distillation. Crushing and extraction processes have also been taught. However, prior art processes have not dealt with the problem of obtaining hydrocarbons from hydrocarbon-containing plants wherein the said hydrocarbons are recovered from a crop in liquid and gaseous form suitable for use as fuel or as chemical feedstocks.

An object of this invention accordingly is to provide a process for production of chemical feedstocks and hydrocarbon fuels from plant sources which permits the effective utilization of whole plant biomass as a raw material source. Another object of this invention is to provide a process for the production of liquid and gaseous hydrocarbons from plant biomass in quantity. Another object is to provide increased production of liquid and gaseous hydrocarbons from renewable natural resources. Another object is to maximize production of liquid and gaseous hydrocarbons with value as chemical feedstocks and as fuels.

These and other objects and advantages of the present invention will become clear from the following specification.

SUMMARY OF THE INVENTION

A process for production and recovery of liquid and gaseous hydrocarbons from hydrocarbon-containing whole plants which are suitable as chemical feedstocks or as fuels wherein pulverized plant biomass is thermally converted in an autothermic furnace at a temperature within the range from about 200° C. to 1000° C. for 1 second to 30 minutes, the resulting liquid and gaseous hydrocarbons are recovered in a condition suitable for use as chemical feedstocks or as hydrocarbon fuels.

DETAILS OF THE INVENTION

The invention relates to a process for producing and recovering liquid and gaseous hydrocarbons from whole plants which are rich in hydrocarbons. Examples of these plants are *Euphorbia heterophylla, Euphorbia lathyrus, Euphorbia marginata, Asclepias syriaca, Calotropis procera,* and *Apocynum sibiricum.* The invented process is not limited to these plants and can be applied to any hydrocarbon-containing plant including those in the Euphorbiaceae, Apocynaceae, Asclepiadaceae, Compositae, Cactaceae and Pinaceae families.

The present invention is directed to a process for the thermal conversion of pulverized biomass in a reducing atmosphere at 200° C. to 1000° C. wherein increased yields of liquid and gaseous hydrocarbons are obtained. The reducing atmosphere is obtained and sustained by the hydrocarbon content of the plant raw material, the oxygen input and the reaction of char with oxygen in the char oxidation zone to produce and maintain the required temperature. Excess oxidation of the hydrocarbon products to less valuable materials is controlled by the presence of the reducing atmosphere. The liquid and gaseous hydrocarbons produced can be used as fuel gases or as feedstocks for chemical manufacture. The excess char is removed to serve as fuel.

FIG. 1 is a schematic illustration of the invention according to which the biomass is thermally converted in a reducing atmosphere to produce hydrogen, methane, acetylene, ethylene, butene, carbon monoxide, etc., and liquids composed of aliphatic, aromatic and functionalized compounds containing nitrogen and oxygen. FIG. 1 depicts a gravity autothermic furnace.

The cracking zone and conversion zone reactions are moderated and controlled by the amount of oxygen introduced into the furnace and the amount of char which is removed. Any suitable amount of oxygen can be used from about 0.1 up to approximately 1 to 2 pounds of oxygen (as molecular oxygen) per pound of char oxidized. Excess quantities of oxygen over the amount required to obtain the required temperature will diminish or eliminate the reducing atmosphere and affect the yield of desired products.

Referring to FIG. 1, the whole-plant biomass is introduced by line 1 to the chopper or grinder 2. Chopped and pulverized material is fed by line 3 to a moving bed furnace 4. The entry to the moving bed furnace 4 by the pulverized biomass is through an airlock feeder 5. The chopped biomass encounters the drying and preheating zone 6 wherein a reducing atmosphere is present at a temperature within the range of from about 100° C. to about 700° C. upon entry into the furnace 4. Air entry into zone 6 is restricted by the compacting of the biomass and the positive pressure developed within the body of the furnace 4, thus maintaining the reducing atmosphere. The dried and heated biomass gravitates into the thermal conversion zone 7 wherein carbon monoxide, methane and other reducing gases as well as carbon dioxide from oxidation zone 8 are present at a temperature within the range of from 200° C. to 1000° C. The product gases from the thermal conversion zone 7 rise through the drying and preheating zone 6 and are removed by line 9. The product gases are passed to a condenser 10 for collection of liquids. Oxygen is introduced into the oxidation zone 8 by line 11. The oxidation zone temperature is within the range of from about 500° C. to about 1000° C. Char and ash are removed by line 12 through an air-lock discharge 13. A positive pressure gradient is maintained within the furnace relative to the exterior of the furnace to prevent entry of air into the furnace and to maintain the reducing atmospheres in the preheating and thermal conversion zones.

The present invention accordingly is directed to a process for the thermal conversion of biomass in a reducing atmosphere wherein increased yields of liquid and gaseous hydrocarbons are obtained from whole plants which contain hydrocarbons at a temperature within the range from about 200° C. to about 1000° C.

Although non-hydrocarbon containing plants can be used as the feed biomass, it is preferred that hydrocarbon containing plants selected from the group consisting of *Euphorbia heterophylla, E. lathyrus, E. marginata, Asclepias syriaca, Calotropis procera* and *Apocynum sibiricum* and other hydrocarbon-producing plants in the Euphorbiaceae, Apocynaceae, Asclepiadaceae, Compositae, Cactaceae and Pinaceae families be utilized as the feed material. Substantially larger quantities of liquid hydrocarbons and gases are produced from these hydrocarbon-containing plants than from non-hydrocarbon containing plants by the invented process.

An essential element of this invention is an autothermic furnace wherein the pulverized whole-plant biomass feed is exposed to temperatures of from 200° C. to about 1000° C. in the thermal conversion zone for a period of from about 1 second to 30 minutes, preferably for a period sufficiently long enough to convert the hydrocarbons contained in the plants to liquids and gaseous products. The furnace is defined as an autothermic furnace wherein combustion of part of the feedstock with preferably oxygen (and less preferably—air) supplies precisely the amount of heat required for thermal conversion of the hydrocarbons contained in the biomass to liquid and gaseous products. The autothermic furnace can be of the moving bed type wherein gravity causes the biomass to progress from one zone to another as a moving bed feed stream. A continuous moving bed furnace dependent upon a rotating bed can also be used.

The gravity autothermic type is preferred. Char from the biomass progresses downward and is removed from the gravity autothermic furnace and can be used as a fuel source. If the temperature and or/residence times are too low, the conversion of hydrocarbon content of the plants is incomplete. When the temperature and/or residence time are too high, the products are thermally degraded and give low yields of usable chemical feedstocks or hydrocarbon fuels because of degradation. Use of excess oxygen results in production of carbon dioxide. An essential element of the present invention accordingly is control of the oxygen feed to maintain a reducing atmosphere at a temperature within the range of from about 100° C. to 1000° C., i.e., from about 100° C. to about 700° C. in the preheating zone and from about 200° C. to about 1000° C. in the thermal conversion zone.

Condensable liquids obtained in thermal conversion of hydrocarbon-containing whole plants are complex mixtures of at least 50 components. They are composed of aliphatic, aromatic and functionalized compounds containing oxygen and nitrogen. In general, these organic liquids are soluble in solvents of moderate polarity and are less soluble in very polar or nonpolar solvents. Elemental composition of organic liquids obtained in thermal conversion of hydrocarbon-containing whole plants (i.e., *E. marginata, E. lathyrus* and *C. procera*) has been determined as being as follows: carbon 70–84(wt)%; hydrogen 5.9–6.8(wt)%; oxygen 10–17(wt)%; nitrogen 2.0–4.1(wt)%. In contrast to the above analyses, nonhydrocarbon-containing whole plants (i.e., sudangrass) have analyzed as follows: carbon 56(wt)%; hydrogen 7.6(wt)%; oxygen 31(wt)%, and nitrogen 1.2(wt)%.

By moving bed feed stream is meant a stream of biomass particles flowing downward through the preheating temperature zone of about 100° C. to about 700° C. and the thermal conversion temperature zone of about 200° C. to about 1000° C. wherein the contained hydrocarbons are thermally driven from the biomass, are cracked and flow upwards through the incoming pulverized biomass feed. The char is partially combusted to serve as a source of heat. The remaining char and ash progress through the furnace (downward in a gravity type) to be removed through an air lock discharge.

The invented process can be carried out in either a batch or continuous type operation. The continuous process is preferred and is as described in the following specification. For continuous operation various reactor designs could be used but use of a vertical shaft moving bed furnace is preferred.

In general, the process of the instant invention in operation is as follows. Whole plant biomass which has been chopped and pulverized to a particle size wherein the cell walls have been ruptured is preheated at a temperature of from about 100° C. to about 700° C. to fully dry the material, if water is present, and to permit control of the chemical reaction in the thermal conversion zone which follows, thereby obtaining optimum desirable product distribution. The dried whole plant biomass is thereupon thermally decomposed in an autothermic furnace (gravity or rotating bed) in a reducing atmosphere with a residence period of 1 second to 30 minutes at a temperature within the range of from about 200° C. to 1000° C. Field-dried whole plants which have been sun-dried to approximately 10–20 (wt) percent water can be used. A higher moisture content can be reduced by lengthening the preheat and drying zone. If sun-drying is not feasible, suitable drying equipment can be used.

The biomass char serves as fuel. The excess char and ash are removed as bottoms from the moving bed furnace vessel. The overhead comprising ethylene and other hydrocarbon gases and liquid condensables is transferred to a condenser wherein the condensable liquids were removed for use as they are or for further thermal cracking to low molecular weight hydrocarbons.

An alternative embodiment utilizes solvent extraction of the whole-plant biomass wherein hydrocarbon-containing biomass is chopped or ground to a suitable particle size for solvent extraction, the particles are percolated in a solvent suitable for solvent extraction such as acetone, butanol, etc. The solvent extract containing hydrocarbon resins is evapoated to dryness, the solvent being recovered. The hydrocarbon resin is thereupon pulverized and fed to the moving bed furnace. The advantage of using hyrocarbon resin extracts as feed is that the amount of usable chemical feedstock such as ethylene and propylene, can be increased as is indicated in the following table. Individual plant biomass can result in differing results. An externally fired reactor (coker) can also be used.

TABLE I

Thermal Conversion of E. Lathyrus Plants - Plant Extracts and Whole Dried Plants at 850° C. Under Helium

|  | Plant Acetone Extracts % (wt) | Whole Dried Plants % (wt) |
| --- | --- | --- |
| Char | 18.3 | 32.0 |
| Liquid | 13.3 | 17.6 |
| Carbon Monoxide | 5.8 | 8.0 |
| Hydrogen | 0.8 | 1.5 |
| Methane | 5.0 | 5.7 |
| Ethylene | 16.7 | 5.0 |
| Ethane | 2.5 | 0.9 |
| Propylene | 5.8 |  |
| Benzene | 4.2 | 1.0 |
| Carbon Dioxide | 27.5 | 27.8 |
| Acetylene | — | 1.0 |
| Total | 100 | 100 |

The raw materials for the process of this invention can be, as stated, the ground or chopped pulverized whole-plant biomass of hydrocarbon-containing plants or the extracted hydrocarbon resins of these plants. The ground or chopped biomass before drying can have a water content varying up to about 98%, the water content of fresh plant materials being about 70 to 98% by weight. For use in the process of this invention the feed materials fed to the autothermic furnace preferably are pulverized wherein the cell walls are ruptured.

Field-dried materials are preferred for economic reasons. However, if field-dried materials are not available the whole plant biomass can be fed into a drier and the moisture content lowered therein to less than 15(25)% and preferably to from 5 to 10(wt)%. It is not essential to the process of this invention that the materials be completely dry before introduction into the furnace.

Any well known drying implement capable of the requirements of the operation can be used within the scope of the invention. A rotary dryer which can use a portion of the hot gases from carbonization of the char produced by the thermal decomposition process is preferred. This gas can be used to heat the whole plant biomass to a temperature of approximately 100° C. to drive off the contained water.

Accordingly whole-plant biomass or biomass hydrocarbon resin extract is fed into an autothermic furnace wherein the preheat temperature is within the range of from about 100° C. to about 700° C. and wherein controlled thermal conversion at a temperature of from about 200° C. to about 1000° C. takes place. The process uses oxygen because any carbon dioxide in the product gases can be removed easily. The use of air or a carrier gas is not preferred as the presence of nitrogen or inert gases in the product gases dilutes the product gases and substantially reduces their heating value. Moreover, the high dilution with nitrogen reduces the potential utility of the product gases as chemical raw materials.

Control of temperature of the autothermic furnace by controlling oxygen input is essential to the process. Use of a high ratio of oxygen to biomass feed creates undesirable conditions within the furnace. With a high oxygen to biomass ratio, the thermal conversion temperature can exceed required temperature ranges, the reducing atmosphere is diminished and production of carbon dioxide and water is maximized. Preferred temperature range minimizes production of carbon dioxide and maximizes a reducing atmosphere and production of organic liquids and gases suitable as chemical feedstocks and as fuels.

An autothermic moving bed furnace is preferred in the process of the instant invention. A vertical shaft autothermic moving bed furnace is preferred as being simplest in conception and lowest in capital cost although a horizontal autothermic moving bed furnace can be used. A rotary autothermic kiln can be used but sealing the discharge and the rotating cylinder from the stationary feed source can be a problem. In the vertical shaft autothermic moving bed furnace, the feed material is fed through the top of the furnace through an airlock. The moving bed vertical autothermic furnace has a drying zone in the top portion, a thermal conversion zone in the middle portion and an oxidation zone in the bottom portion where the char is burned to produce heat. The feed material compacts the feed passing through the airlock and prevents the admittance of air. Generated product gases pass upward through the shaft and are removed near the top of the furnace. A char discharge airlock at the base of the furnace permits removal of char generated within the furnace. Temperature control is maintained by monitoring the oxygen to biomass ratio with required instrumentation.

Generated product gases are passed through a condenser in order to trap liquid products. Gaseous products are collected in a container designed for this purpose. The condenser can use commercially available technology with precautions taken to avoid fouling due to tar buildup and with short contact time to stop further chemical reactions.

In the alternative embodiment, plant extracts for which this process can be used include those from the Euphorbiaceae, Asclepiadaceae, Cactaceae, Apocynaceae, Pinaceae, and Compositeae families although the invention is applicable to any plant-derived hydrocarbon resin. Fresh plants are extracted with acetone, cyclohexane, benzene or any other solvent of choice. The solvent is evaporated and the extracts are thermally converted at temperatures from 200° C. to 1,000° C. Preheating of the extract at temperatures of 200° C. to 700° C. permits control of the chemical reaction at the thermal conversion temperature which follows, thus obtaining optimum desirable product distribution.

The potential of this recovery method is to obtain gaseous and liquid hydrocarbons such as methane, ethane, ethylene, acetylene, ethane, propylene, benzene, as well has hydrogen from plants rich in hydrocarbons. The liquid fraction can be used as is or recycled for further cracking to low molecular weight products. Carbon dioxide produced in the process can be easily removed from the product stream by conventional absorption technology.

Embodiments of the present invention may be found in the following examples. Helium was used to maintain the equivalent of a reducing atmosphere. These embodiments and examples are presented for purposes of illustration only and are not intended to limit the scope of the invention.

EXAMPLE I

The following example simulates an autothermic moving bed furnace wherein the feed material progresses through a drying zone and thence to a thermal conversion zone.

1.00 g portion of E. lathyrus was ground, placed in a boat and inserted into a preheating zone at 630° C. to remove water present. Helium gas was used to exclude oxygen, thereby providing a reducing atmosphere to carry the volatilized and partially thermally converted material to the reaction zone which was heated to 950° C. Residence time was 4 seconds. Liquid products were trapped in a container cooled with dry ice-acetone and gases were collected in a special plastic container. The yield of char was 33.3 percent and the yield of liquid products was 4.5 percent. The gaseous mixture was analyzed by mass spectroscopy and the yields calculated from the total amount of gases collected. The yield of carbon monoxide was 8.3%, carbon dioxide 19.8 percent, methane 6.4 percent, acetylene 1.1 percent, ethylene 6.1 percent, and benzene 1.4 percent among other gaseous products. Total hydrocarbon yield was 21.0 percent based on dry weight of the starting plant material. The carbon dioxide produced was an indication of oxygen in the plant biomass feed.

EXAMPLE II

A 1.0 g sample of dried E. marginata was thermally converted as described in Example I employing a temperature of 950° C. the yield of char was 31.1%, liquid products 12.6%, carbon monoxide 13.3%, carbon dioxide 17.7%, methane 3.9% acetylene 1.1%, and ethylene 4.0%. Total hydrocarbon yield was 21.6%.

EXAMPLE III

A 1.0 g sample of dried *A. syriaca* was thermally converted as described in Example I employing a temperature of 950° C. The yield of char was 27.7%, liquid products 7.7%, carbon monoxide 5.7%, carbon dioxide 8.5%, methane 6.0%, acetylene 0.8%, ethylene 4.5% and benzene 0.5%. Total hydrocarbon yield was 18.2%.

EXAMPLE IV

A 1.00 g sample of dried Sudangrass was thermally converted as described in Example I employing a temperature of 950° C. The yield of char was 32.0%, liquid products 6.5%, carbon monoxide 14.2%, carbon dioxide 12.9%, methane 3.6% and ethylene 3.2%. Total hydrocarbon yield was 14.4%.

EXAMPLE V

A 1.00 g sample of dried corn stovers was thermally converted as described in Example I employing a temperature of 950° C. The yield of char was 28.3%, liquid products 8.9%, carbon monoxide 16.8%, carbon dioxide 13.5%, methane 3.8% and ethylene 3.3%. Total hydrocarbon yield was 17.1%.

EXAMPLE VI 1.00 g samples of hydrocarbon-containing plants of *E. lathyrus, G. Squarrosa, E. marginata, A. syriaca* and *C. procera* were thermally converted as described in Example I. 1.00 g samples of nonhydrocarbon containing dried plants of *S. sudanense, H. tuberosus* and corn stovers were also thermally converted. The results are shown in Table II. The data are averages of two runs.

TABLE II

Hydrocarbon-Containing and Non-Hydrocarbon Containing Plants - Thermal Conversion at 950° C. Under Helium

| Hydrocarbon Containing | Char wt % | Organic Liquids wt % (A) | Hydrocarbon Gases wt % (B) | Total Cols. A & B wt % |
|---|---|---|---|---|
| E. lathyrus | 32.6 | 6.3 | 14.0 | 20.3 |
| E. marginata | 28.9 | 12.6 | 9.0 | 21.6 |
| G. squarrosa | 28.6 | 9.1 | 10.2 | 19.3 |
| A. syriaca | 27.7 | 7.8 | 10.5 | 18.3 |
| C. procera | 31.7 | 11.0 | 7.5 | 18.5 |
| Averages | 29.9 | 9.5 | 10.6 | 19.8 |
| Non-Hydrocarbon Containing | | | | |
| S. sudanense | 31.5 | 6.8 | 7.9 | 14.7 |
| H. tuberosus | 37.2 | 7.9 | 6.9 | 14.8 |
| Corn Stovers | 27.3 | 8.2 | 8.2 | 16.4 |
| Averages | 32.0 | 7.6 | 7.7 | 16.0 |

| Hydrocarbon Containing | Total Cols. A & B wt % | Calc.* Total BTU/lb | Calc.* Total BTU/ft³ Gaseous Products |
|---|---|---|---|
| E. lathyrus | 20.3 | 15,100 | 595 |
| E. marginata | 21.6 | 13,000 | — |
| G. squarrosa | 19.3 | — | 593 |
| A. syriaca | 18.3 | — | 573 |
| C. procera | 18.5 | 13,900 | — |
| Averages | 19.8 | | 587 |
| Non-Hydrocarbon Containing | | | |
| S. sudanense | 14.7 | 10,450 | 515 |
| H. tuberosus | 14.8 | — | — |
| Corn Stovers | 16.4 | — | 506 |
| Averages | 16.0 | | 510 |

*Calculated: based on standard heats of combustion, Handbook of Chem., Lange, 10th Ed., McGraw-Hill, N.Y., 1961

The above data indicate the relative increased yield of hydrocarbon gases and organic liquids from hydrocarbon containing plants versus non-hydrocarbon containing plants. The data are not considered to be directly comparable but are considered to indicate approximate relative yields and increased availability of products suitable for fuel use as obtained by the instant process.

EXAMPLE VII

The following example simulates an autothermic moving bed furnace wherein the hydrocarbon extract feed material progresses through a drying zone and thence to a thermal conversion zone.

A 1.0 g portion of *E. lathyrus* cyclohexane extract was inserted into a preheating zone at 620° C. Helium gas was used to exclude oxygen-containing gases, thereby providing a reducing atmosphere, and as the carrier gas. The reaction zone was heated to 800° C. The volatilized sample was passed through the reaction zone with a residence time of 4 seconds. Liquid products were trapped in a container cooled with dry ice-acetone and gases were collected in a special plastic container. The yield of char was 17.7 percent and liquid fraction was obtained in 10.9 percent yield. Collected gases were analyzed by mass spectroscopy and yields calculated from the total amount of gases collected. The yield of carbon monoxide was 6.1 percent, carbon dioxide 18.9 percent, methane 4.7 percent, ethylene 16.5 percent, ethylene 16.5 percent, ethane 2.4 percent, propylene 5.6 percent, butenes 2.2 percent and benzene 4.2 percent.

EXAMPLE VIII

A 1.00 g portion of *Grindelia squarrosa* acetone extracts was thermally converted as described in Example VII employing a preheater temperature of 600° C. The yield of char was 3.7 percent, liquid fraction 26.0 percent, carbon monoxide 2.2 percent, carbon dioxide 13.4 percent, methane 8.9 percent, ethylene 11.7 percent, ethane 1.9 percent, propylene 4.9 percent, and benzene 1.7 percent.

EXAMPLE IX

A 1.00 g portion of *A. syriaca* acetone extracts was thermally converted as described in Example VII. Preheater temperature was 600° C. The yield of char was 5.5 percent, liquid products 11.4 percent, carbon monoxide 1.5 percent, carbon dioxide 7.9 percent, methane 10.3 percent, ethylene 20.7 percent, ethane 3.0 percent, propylene 7.6 percent, and benzene 1.3 percent.

Details are shown in Table II of Examples VII-IX. As shown in Table II, the amount of char varied from as low as 4–5 percent for *G. squarrosa* and *A. syriaca* to 25 percent for *E. tirucalli*. The yield of liquid products ranged from 10 to 30 percent. Preheater temperature was 600° C. Thermal conversion of *E. lathyrus* extracts at various temperatures showed increasing yields of liquid products with decreasing temperatures. The liquids are complex mixtures, hydrocarbon in nature, having both aromatic and aliphatic components. The composition of gaseous products and yields of gaseous hydrocarbons vary from plant to plant. Best yields of ca. 40 percent hydrocarbon gases were obtained from *A. syriaca* extracts. Total hydrocarbon yields (liquid fraction plus hydrocarbon gases) for the plants studied ranged from 40 to 55 percent.

TABLE II

Thermal Conversion of Plant Extracts at 4 Seconds

| No. | Plant | Temp. (°C.) | Char (wt %) | Organic Liquid Fraction (wt %) | Yield Hydrocarbon Gases Plus Organic Liquids (wt %) |
|---|---|---|---|---|---|
| 115 | E. lathyrus | 950 | 17.9 | 17.1 | 43.3 |
| 116 | E. lathyrus | 950 | 17.2 | 12.9 | 49.9 |
| 117 | E. lathyrus | 800 | 19.0 | 11.5 | |
| 118 | E. lathyrus | 800 | 17.7 | 10.9 | 46.5 |
| 119 | E. lathyrus | 600 | 17.5 | 32.5 | |
| 120 | E. lathyrus | 600 | 18.1 | 33.4 | 51.4 |
| 137 | E. heterophylla | 800 | 18.1 | 39.9 | 58.2 |
| 138 | E. heterophylla | 800 | 16.3 | 23.6 | 45.4 |
| 140 | E. tirucalli | 800 | 24.7 | 22.5 | 38.6 |
| 141 | E. tirucalli | 800 | 26.1 | 27.7 | 43.9 |
| 142 | Grindelia/squarrosa | 800 | 3.7 | 26.0 | 55.1 |
| 143 | Grindelia/squarrosa | 800 | 4.3 | 23.2 | 50.6 |
| 144 | Apocynum sibiricum | 800 | 18.2 | 12.5 | 39.2 |
| 145 | Apocynum sibiricum | 800 | 14.8 | 11.8 | 43.2 |
| 146 | Asclepias tuberosa | 800 | 23.2 | 20.8 | 37.6 |
| 147 | Asclepias tuberosa | 800 | 22.6 | 25.8 | 44.2 |
| 150 | E. marginata | 800 | 18.1 | 26.0 | 46.6 |
| 151 | E. marginata | 800 | 18.8 | 26.8 | 47.1 |
| 156 | A. syriaca | 800 | 4.7 | 10.0 | |
| 157 | A. syriaca | 800 | 5.5 | 11.4 | 54.3 |

EXAMPLE X

An embodiment of the instant invention is as follows:
*E. lathyrus* plants are treated in the following manner.

A vertical moving bed furnace is used corresponding to the diagram in FIG. 1.

*E. lathyrus* biomass of a moisture content of under 20 (wt) % is ground to a suitable particle size in a separate grinder or chopper. The ground *E. lathyrus* biomass is fed to the moving bed furnace through an airlock at the top of the furnace. Oxygen in controlled amounts is fed into the oxidation zone at the bottom of the furnace. The amount of oxygen fed is controlled by analysis of the exit gases.

Calculated BTU value of net gaseous products of moving bed furnace using *E. lathyrus* as feed is about 590–600 BTU/cubic feet.

What is claimed is:

1. A process using whole-plant biomass for production of fuel gases and organic liquids suitable for use as hydrocarbon fuels and as chemical feedstocks which comprises:
   (a) feeding a ground or chopped whole-plant biomass of a suitable particle size to an autothermic furnace containing a heating and drying zone, a thermal conversion zone and an oxidation zone wherein said furnace is a moving bed furnace and means are provided for exclusion of oxygen-containing gases from the inlet port,
   (b) heating and drying said biomass with reducing gases at a temperature within the range of from about 100° C. to 700° C.,
   (c) removing said biomass from said heating and drying zone to said thermal conversion zone wherein a reducing atmosphere is present at a temperature of 200° C. to 1000° C.,
   (d) exposing said biomass in thermal conversion zone to said temperature for a period of 1 second to 30 minutes,
   (e) removing said biomass from thermal conversion zone to oxidation zone wherein said biomass is partially oxidized to char at a temperature of 500° C. to 1000° C. in the presence of oxygen-containing gases selected from the group consisting of molecular oxygen and air,
   (f) removing said biomass from said oxidation zone wherein means are provided for exclusion of oxygen-containing gases from the outlet port,
   (g) removing product gases from heat and drying zone,
   (h) recovering liquid condensables from product gases.

2. The process of claim 1 wherein the ratio of said oxygen-containing gases to said biomass oxidized to char is within the range of from about 0.1 to about 2 pounds of oxygen as molecular oxygen per pound of char oxidized.

3. The process of claim 2 wherein said oxygen-containing gas is molecular oxygen.

4. The process of claim 1 wherein said autothermic furnace is a gravity autothermic furnace.

5. The process of claim 1 wherein said autothermic furnace is a rotating bed autothermic furnace.

6. The process of claim 1 wherein the said biomass comprises hydrocarbon-containing plants selected from the group of plant families consisting of Euphorbiaceae, Asclepiadaceae, Cactaceae, Apocynaceae, Pinaceae and Compositae families.

7. The process of claim 1 wherein said hydrocarbon-containing plants are selected from the group consisting of *Euphorbia heterophylla, Euphorbia lathyrus, Euphorbia marginata, Asclepias syriaca, Calotropis procera* and *Apocynum sibiricum*.

8. A process for production of fuel gases and organic liquids suitable for use as hydrocarbon fuels and as chemical feedstocks from hydrocarbon-containing biomass which process comprises:
   (a) grinding or chopping hydrocarbon-containing biomass to a particle size suitable for solvent extraction,
   (b) percolating said particles in a solvent suitable for hydrocarbon extraction to form a solvent extract of said hydrocarbon-containing biomass,
   (c) evaporating solvent from said solvent extract to obtain hydrocarbon resin extract,
   (d) feeding said hydrocarbon resin extract chopped or ground to a suitable particle size to an autothermic furnace containing a heating zone, a thermal conversion zone and an oxidation zone wherein means are provided for exclusion of oxygen-containing gases from inlet port,
   (d) heating said hydrocarbon resin extract with reducing gases at a temperature within the range from about 100° C. to 700° C.,
   (e) removing said hydrocarbon resin extract from said heating zone to said thermal conversion zone wherein a reducing atmosphere is present at a temperature from about 200° C. to 1000° C.,
   (f) exposing said hydrocarbon resin extract in said thermal conversion zone to said temperature for a period of from about 1 second to 30 minutes, (g) removing said hydrocarbon resin extract from said thermal conversion zone to said oxidation zone wherein said hydrocarbon resin extract is partially oxidized to char at a temperature of from about 50° C. to about 1000° C. in presence of oxygen-containing gases selected from the group consisting of molecular oxygen and air, (h) removing ash and char from said hydrocarbon resin extract from said oxidation zone wherein means are provided for exclusion of oxygen-containing gases from the outlet port, (f) removing product gases from heating zone, (j) recovering liquid condensables from product gases.

9. The process of claim 8 wherein the ratio of said oxygen-containing gases to said hydrocarbon resin extract oxidized to char in said oxidation zone is within the range of from about 0.1 to about 2 pounds of oxygen as molecular oxygen per pound of hydrocarbon resin extract oxidized.

10. The process of claim 9 wherein said oxygen-containing gas is molecular oxygen.

11. The process of claim 8 wherein said autothermic furnace is a gravity autothermic furnace.

12. The process of claim 8 wherein said autothermic furnace is a rotating bed autothermic furnace.

13. The process of claim 8 wherein said hydrocarbon-containing biomass comprises hydrocarbon-containing plants selected from the group of plant families consisting of Euphorbiaceae, Asclepiadaceae, Cactaceae, Apocynaceae, Pinaceae, and Compositae families.

14. The process of claim 13 wherein said hydrocarbon-containing plants are selected from the group consisting of *Euphorbia heterophylla, Euphorbia lathyrus, Euphorbia marginata, Asclepias syriaca, Calotropis procera, Apocynum sibiricum, Grindelia squarrosa, Euphorbia tirucalli,* and *Asclepias tuberosa.*

* * * * *

UNITED STATES PATENT OFFICE
CERTIFICATE OF CORRECTION

Patent No. 4,313,011  Dated January 26, 1982

Inventor(s) Thomas A. Weil, Peter M. Dzadzic, Chien-Cheng J. Shih, and Michael C. Price It is certified that error appears in the above-identified patent and that said Letters Patent are hereby corrected as shown below:

| Column | Line | |
|---|---|---|
| 7 | 7 | "15(25)%" should read --15(wt)-- |
| 8 | 8 | "Compositeae" should read --Compositae-- |
| 10 | 39 | "ethylene 16.5 percent" appears twice. Should appear only once. |
| Claim 8 (g) | | |
| 13 | 4 | "50°C should read --500°C-- |
| 13 | 13 | "(f) removing product" should read --(i) removing product-- |

Signed and Sealed this

Twenty-seventh Day of July 1982

[SEAL]

Attest:

Attesting Officer

GERALD J. MOSSINGHOFF

Commissioner of Patents and Trademarks